United States Patent [19]

Sieber

[11] Patent Number: 4,476,230

[45] Date of Patent: Oct. 9, 1984

[54] PROCESS FOR THE KINETIC DETERMINATION OF IMMUNOCOMPLEXES

[75] Inventor: Axel Sieber, Marburg an der Lahn, Fed. Rep. of Germany

[73] Assignee: Behringwerke Aktiengesellschaft, Marburg an der Lahn, Fed. Rep. of Germany

[21] Appl. No.: 233,985

[22] Filed: Feb. 12, 1981

[30] Foreign Application Priority Data

Feb. 14, 1980 [DE] Fed. Rep. of Germany ....... 3005417

[51] Int. Cl.³ ............................................. G01N 33/54
[52] U.S. Cl. ................................... 436/507; 436/517; 436/513; 436/536; 436/805
[58] Field of Search ................... 23/230 B; 424/8, 11, 424/12, 13; 436/506, 507, 513, 517, 536, 805

[56] References Cited

U.S. PATENT DOCUMENTS 4,205,954  6/1980  Babson .............................. 424/12 X
4,268,171  5/1981  Sternberg ........................... 23/230 B

OTHER PUBLICATIONS

Sieber et al., Proc. Protides of Biol. Fluids, Coll. vol. 23, 1976, pp. 295–298.
Williams, Methods in Immunol. & Immunochem. vol. III, Acd. Press 1971, pp. 19,20.
Tengerdy, Nature, vol. 210, May 14, 1966, pp. 708–710.
Smith, Biochem. vol. 14, 1975, pp. 1496–1502.

Primary Examiner—Sidney Marantz
Assistant Examiner—K. S. McCowin
Attorney, Agent, or Firm—Curtis, Morris & Safford

[57] ABSTRACT

A process for the detection and for the determination of immunocomplexes in liquids is described. It is based on determining the rate at which the immunoglobulin or the antigen present in the complex reacts with an appropriate immuno-partner, and relating this rate to the rate at which this immunoglobulin or antigen reacts with the corresponding immuno-partner in an immunocomplex-free liquid.

1 Claim, No Drawings

PROCESS FOR THE KINETIC DETERMINATION OF IMMUNOCOMPLEXES

The invention relates to a process for the detection and for the determination of immunocomplexes in liquids.

Processes for the detection and for the determination of immunocomplexes (IC) in blood serum are already known. These methods have the disadvantage that they are inaccurate, unreliable, non-specific or expensive. Thus, Helmke et al., Immunität and Infektion 6, 173 (1978), describe a method in which the turbidity of the serum is measured in a laser nephelometer, polyethylene glycol (PEG) is added, the mixture is centrifuged and the turbidity of the supernatant liquor is measured. If the difference between the two turbidity values is sufficiently large, it is said to be possible to determine the amount of immunocomplexes therefrom. However, it is known that polyethylene glycol also precipitates other proteins in addition to the immunocomplexes, and the method thus has a low specificity.

An immunocomplex is composed of an antigen component and an immunoglobulin component, which is an immunoglobulin A, G and/or M. In immunocomplexes of humans, the immunoglobulin component naturally comprises human IgG, IgA and/or IgM, against which specific antibodies can be produced in animals, and isolated, in a known manner.

It has now been found, surprisingly, that the rate at which such a specific antibody reacts against one of the human immunoglobulins varies, depending on whether the human immunoglobulin is free or bonded in an immunocomplex. In most cases, the antibody reacts more slowly with the immunoglobulin when this is bonded in an immunocomplex than when it is free.

The rate at which an antibody reacts with the associated antigen can be determined in a manner known per se, for example from the increase, with respect to time, in the absorption of light in a photometer or in the turbidity in a nephelometer. For this determination, it is possible to use a recorder with which the particular measuring signal, as a function of time, is recorded with a pen or displayed on a screen or which enables the measurement data to be processed immediately by a computer.

The process according to the invention comprises a procedure in which the rate at which in each case an antibody specific for one of the human immunoglobulins G, A or M reacts with its antigen in the serum sample is related to the rate at which the same antibody reacts with its antigen in an immunocomplex-free reference serum, in which the corresponding antigen is present in the same concentration as in the serum sample to be investigated. The rate at which an antibody directed against one of the three human immunoglobulin types reacts with its corresponding immunoglobulin type is generally lower, but in case of IgM antibodies higher, if this immunoglobulin type is bonded in an immunocomplex than the rate of reaction when this immunoglobulin type is not in the form of an immunocomplex. This difference in the rate of reaction is observed in the initial phase of the reaction, whereas the rates become approximately the same in the course of the reaction, independently of whether the immunoglobulin is bonded in an immunocomplex or is free.

From the statements hitherto made, it can already be seen that the rate at which an antibody directed against one of the human immunoglobulin types reacts with its antigen is only changed if all or some of its antigen is bonded in an immunocomplex. It is thus simultaneously indicated which of the three immunoglobulin types is or are completely or partly bonded in an immunocomplex. With the immunoglobulins G or A there were always observed retarded kinetics, whereas the IgM exhibited partially retarded and partially more rapid kinetics.

It has furthermore been found that the rate at which the antigen present in the immunocomplex reacts with an antibody directed specifically against this antigen is likewise reduced. This discovery can similarly be used for the determination of the amount of immunocomplexes present in a liquid. This embodiment of the process according to the invention is of interest, for example, in autoimmunity disorders in which the immunocomplexes contain endogenous proteins as the antigen.

The process for the detection and for the determination of the amount of immunocomplexes in a liquid comprises determining the rate at which the immunoglobulins G, A and M present in this liquid or at which the antigen present in the immunocomplex in each case react with an appropriate specific antibody, and relating this rate to that which is determined when the antibody reacts with the immunoglobulin or the antigen, when the immunoglobulin or the antigen is present in an immunocomplex-free liquid. The rate is appropriately determined from the proportional section of the titration curve.

A standard solution, for example the serum of a healthy blood donor or a mixture of sera of healthy blood donors containing no immunocomplexes, can be used as the immunocomplex-free liquid.

The process is described in the following text by way of example:

The concentrations of IgG, IgA and IgM in the liquid to be investigated are determined with the aid of a method for the quantitative determination of proteins, for example radial immunodiffusion (RID), laser nephelometry (LN) or turbidimetry (TM). In the case of the optical methods LN and TM, the concentration is determined from the section of the titration curve in which the rate of reaction tends towards O and the curve in the customary representation becomes horizontal. Such a process is also known as the end point process. Three dilutions of a normal reference serum in which no immunocomplexes are present but of which the concentrations of IgG, IgA and IgM are known are prepared such that in each case one has the same concentration of IgG, IgA and IgM as has been measured in the solution to be investigated.

A particular amount of an antiserum specific for human immunoglobulin G, A or M or for the antigen present in the immunocomplex is added in each case to one sample of the liquid, in a suitable dilution, to be investigated for immunocomplexes and the rate of the immunochemical reaction is determined. The corresponding dilutions of the reference serum in which the immunoglobulins or the antigen are present in the same concentration as in the liquid to be investigated are treated in the same manner.

The amount of immunocomplex is determined from the difference in the rates of reaction in the liquid to be investigated and in the reference serum.

In a preferred embodiment, the reaction kinetics of the reaction between the antibody and the immunoglobulin or antigen are plotted. The end point of the reaction is generally reached after 30 minutes. The reaction with the corresponding dilution of the reference serum is measured in the same manner and the curve for the reaction kinetics is preferably plotted over the corresponding curve for the liquid to be investigated.

If the liquid to be investigated contains no immunocomplexes, the curve pairs for the liquid to be investigated and the reference liquid are congruent. If immunocomplexes are present, at least one of the curves deviates from the curve of the reference serum. The kinetic curve for the appropriate reaction in the liquid to be investigated then has a lower or, for IgM sometimes higher, gradient than the reference curve, the difference between the gradients being a measure of the amount of immunocomplex present. Exceptions may occur with IgM-containing immunocomplexes characterized by higher gradients. Similar results are obtained if synthetic immunocomplexes, for example of tetanus toxoid and the corresponding human antibodies, which have been mixed with an immunocomplex-free serum, or aggregated IgG, which, as is known, is very similar to immunocomplexes in respect of its physicochemical and immunochemical properties, are used instead of natural immunocomplexes.

The invention is illustrated by the following examples:

EXAMPLE 1

Measurement of the IC in serum from a patient 1,090 mg/dl of IgG, 825 mg/dl of IgA and 137 mg/dl of IgM were measured in serum from a patient with the aid of laser nephelometry (LN). The serum from the patient was diluted with physiological NaCl solution in the ratio 1:100, and in each case 200 $\mu$l of a specific antiserum, diluted in the ratio 1:5, for human IgG, IgA or IgM were added to, in each case, 100 $\mu$l of the serum dilution and the reaction kinetics of the turbidity arising as a result of the increase in the immunocomplexes were measured in a laser nephelometer over a period of 30 minutes.

An IC-free reference serum contained 1,154 mg/dl of IgG, 233 mg/dl of IgA and 187 mg/dl of IgM. The serum was diluted in a ratio of 1:107 for the kinetic measurement of IgG, in a ratio of 1:28 for the kinetic measurement of IgA and in a ratio of 1:136 for the kinetic measurement of IgM, so that, in the appropriate batch, the three proteins were present in the same concentrations as in the serum from the patient. 100 $\mu$l of the serum dilution was likewise reacted with 200 $\mu$l of the antiserum dilution and the kinetics were measured with a laser nephelometer. In the case of IgA, the curve obtained from the kinetic measurements showed a significantly flatter gradient in the region of the highest rate of reaction, compared with the reference serum. In the case of the two other proteins, the curves for the sample and the reference serum followed an identical course. The clinical findings and comparison tests with other methods confirm the presence of IC.

EXAMPLE 2

Measurement of synthetic immunocomplexes

A Heidelberger curve was first obtained in a laser nephelometer by mixing a dilution series of tetanus antibodies of human origin with tetanus toxoid in order to obtain, by titration, the region of antigen excess in which soluble ICs were present. Under the conditions given, this was the case for a mixture of 180 LF/ml of toxoid and 50 IU/ml of antibodies.

The appropriate proportions were introduced into an IC-free human serum, which now contained synthetic human immunocomplexes. The same negative human serum was used as a reference serum by adding the same amount of tetanus antibodies only to another sample.

It was thus ensured that the IC serum and reference sample contained the same concentrations of IgG, IgA and IgM.

The remaining experimental procedure corresponds to that in Example 1.

The measurement showed the presence of IC for IgG and IgA, whereas IgM-IC could not be detected.

EXAMPLE 3

Model reaction with aggregated IgG

An IC-free human serum was warmed to 63° C. for 15 minutes in order to subject the IgG contained therein to heat aggregation. The serum was then diluted in the ratio 1:100 and subjected to further investigation as described in Example 1. In this case, the same serum which had not been subjected to heat treatment was used as the reference serum. It was found that the aggregated IgG, analogously to IC, exhibited delayed kinetics in the reaction with a specific antiserum.

I claim:

1. A method for detecting and determining the amount, in a liquid, of an immunocomplex of an immunoglobulin selected from the group consisting of immunoglobulins G, A, and M, which method comprises determining the rate at which said immunocomplex reacts with an antibody for the immunoglobulin present in said immunocomplex, and comparing this rate with the rate of reaction of said antibody with said immunoglobulin present in a liquid free of any immunocomplex of said immunoglobulin.

* * * * *